(12) United States Patent
Ashby et al.

(10) Patent No.: US 8,317,821 B1
(45) Date of Patent: Nov. 27, 2012

(54) RELEASE MECHANISM

(75) Inventors: Mark Ashby, Laguna Niguel, CA (US); Eduardo Chi Sing, Dana Point, CA (US); Luis R. Urquidi, Oceanside, CA (US); Tin Tran, Anaheim, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1651 days.

(21) Appl. No.: 10/462,064

(22) Filed: Jun. 12, 2003

Related U.S. Application Data (63) Continuation-in-part of application No. 10/287,922, filed on Nov. 4, 2002, now Pat. No. 7,455,680, and a continuation-in-part of application No. 10/462,065, filed on Jun. 12, 2003, now Pat. No. 7,695,492, and a continuation-in-part of application No. 10/461,587, filed on Jun. 12, 2003, now Pat. No. 7,955,353.

(51) Int. Cl.
*A61B 17/03* (2006.01)

(52) U.S. Cl. ........................................ 606/213; 606/108

(58) Field of Classification Search .......... 606/191–200, 606/108, 213–215; 600/585; 604/533–535, 604/96.01, 13–15
See application file for complete search history.

(56) References Cited

U.S. PATENT DOCUMENTS

| | | | |
|---|---|---|---|
| 581,235 A | 4/1897 | Kenyon |
| 1,578,517 A | 3/1926 | Hein |
| 2,086,580 A | 7/1937 | Shirley |
| 2,465,357 A | 3/1949 | Correll |
| 2,492,458 A | 12/1949 | Bering, Jr. |
| 2,507,244 A | 5/1950 | Correll |
| 2,558,395 A | 6/1951 | Studer |
| 2,597,011 A | 5/1952 | MacMasters et al. |
| 2,680,442 A | 6/1954 | Linzmayer |
| 2,761,446 A | 9/1956 | Reed |
| 2,814,294 A | 11/1957 | Figge |
| 2,824,092 A | 2/1958 | Thompson |
| 2,899,362 A | 8/1959 | Sieger, Jr. et al. |
| 3,157,524 A | 11/1964 | Artandi |
| 3,724,465 A | 4/1973 | Duchane |
| 4,000,741 A | 1/1977 | Binard et al. |
| 4,077,409 A | 3/1978 | Murray et al. |
| 4,211,323 A | 7/1980 | Olsen |

(Continued)

FOREIGN PATENT DOCUMENTS

EP 0032826 7/1981

(Continued)

OTHER PUBLICATIONS

Sanborn, Timothy A., Brinker, Jeffrey A., Kosinski, Edward J. Percutaneous Collagen Hemostatic Device. J Am Coll Cardiology, 1993, vol. 22: 1273-9.*

(Continued)

*Primary Examiner* — Kathleen Sonnett
(74) *Attorney, Agent, or Firm* — Seager, Tufte & Wickhem LLC (57) ABSTRACT

The present invention provides for a method and apparatus related to a releasable mechanism having a first connector having a first end and a second end, a second connector having a top and a bottom, a first notch positioned near the first connector second end to releasably mate with the second connector bottom, and a second notch located near the second connector bottom to releasably receive the first connector second end.

10 Claims, 7 Drawing Sheets

U.S. PATENT DOCUMENTS

| | | |
|---|---|---|
| 4,218,155 A | 8/1980 | Weidner |
| 4,238,480 A | 12/1980 | Sawyer |
| 4,292,972 A | 10/1981 | Pawelchak |
| 4,323,072 A | 4/1982 | Rosenbluth et al. |
| 4,340,066 A | 7/1982 | Shah |
| 4,390,018 A | 6/1983 | Zuloowski |
| 4,404,970 A | 9/1983 | Sawyer |
| 4,515,637 A | 5/1985 | Cioca |
| 4,587,969 A | 5/1986 | Gillis |
| 4,588,395 A | 5/1986 | Lemelson |
| 4,619,261 A | 10/1986 | Guerriero |
| 4,619,913 A | 10/1986 | Luck et al. |
| 4,645,488 A | 2/1987 | Matukas |
| 4,708,718 A | 11/1987 | Daniels |
| 4,744,364 A | 5/1988 | Kensey |
| 4,790,819 A | 12/1988 | Li et al. |
| 4,829,994 A | 5/1989 | Kurth |
| 4,850,960 A | 7/1989 | Grayzel |
| 4,852,568 A | 8/1989 | Kensey |
| 4,890,612 A | 1/1990 | Kensey |
| 4,900,303 A | 2/1990 | Lemelson |
| 4,929,246 A | 5/1990 | Sinofsky |
| 4,936,835 A | 6/1990 | Haaga |
| 4,950,234 A | 8/1990 | Fujioka et al. |
| 5,007,895 A | 4/1991 | Burnett |
| 5,021,059 A | 6/1991 | Kensey et al. |
| 5,053,046 A | 10/1991 | Janese |
| 5,061,274 A | 10/1991 | Kensey |
| 5,080,655 A | 1/1992 | Haaga |
| 5,108,421 A | 4/1992 | Fowler |
| 5,163,904 A | 11/1992 | Lampropoulos et al. |
| 5,167,624 A | 12/1992 | Butler et al. |
| 5,192,300 A | 3/1993 | Fowler |
| 5,192,301 A | 3/1993 | Kamiya et al. |
| 5,195,988 A | 3/1993 | Haaga |
| 5,220,926 A | 6/1993 | Jones |
| 5,221,259 A | 6/1993 | Weldon et al. |
| 5,242,683 A | 9/1993 | Klaveness |
| 5,250,071 A * | 10/1993 | Palermo ............... 606/198 |
| 5,275,616 A | 1/1994 | Fowler |
| 5,282,827 A | 2/1994 | Kensey et al. |
| 5,290,310 A * | 3/1994 | Makower et al. ............ 606/213 |
| 5,310,407 A | 5/1994 | Casale |
| 5,322,515 A | 6/1994 | Karas et al. |
| 5,324,306 A | 6/1994 | Makower et al. |
| 5,325,857 A | 7/1994 | Nabai et al. |
| 5,334,216 A | 8/1994 | Vidal et al. |
| 5,366,480 A | 11/1994 | Corriveau et al. |
| 5,370,656 A | 12/1994 | Shevel |
| 5,380,270 A * | 1/1995 | Ahmadzadeh ............... 604/9 |
| 5,383,896 A | 1/1995 | Gershony et al. |
| 5,383,899 A | 1/1995 | Hammersiag |
| 5,385,550 A | 1/1995 | Su et al. |
| 5,388,588 A | 2/1995 | Nabai et al. |
| 5,391,183 A | 2/1995 | Janzen et al. |
| 5,417,699 A | 5/1995 | Klein et al. |
| 5,417,708 A * | 5/1995 | Hall et al. ............... 606/200 |
| 5,419,765 A | 5/1995 | Weldon et al. |
| 5,431,639 A | 7/1995 | Shaw |
| 5,437,292 A | 8/1995 | Kipshidze |
| 5,437,631 A | 8/1995 | Janzen |
| 5,443,481 A | 8/1995 | Lee |
| 5,467,780 A | 11/1995 | Nabai et al. |
| 5,478,352 A | 12/1995 | Fowler |
| 5,479,936 A | 1/1996 | Nabai et al. |
| 5,486,195 A | 1/1996 | Myers |
| 5,490,736 A | 2/1996 | Haber |
| 5,522,840 A | 6/1996 | Krajicek |
| 5,522,850 A | 6/1996 | Yomtov et al. |
| 5,526,822 A | 6/1996 | Burbank et al. |
| 5,527,332 A | 6/1996 | Clement |
| 5,529,577 A | 6/1996 | Hammershiag |
| 5,540,715 A | 7/1996 | Katseros et al. |
| 5,542,914 A | 8/1996 | Van Iten |
| 5,545,178 A | 8/1996 | Kensey et al. |
| 5,554,108 A | 9/1996 | Browning et al. |
| 5,558,853 A | 9/1996 | Quay |
| 5,591,204 A | 1/1997 | Janzen et al. |
| 5,591,205 A | 1/1997 | Fowler |
| 5,601,602 A | 2/1997 | Fowler |
| 5,601,603 A | 2/1997 | Illi |
| 5,645,566 A | 7/1997 | Brennenman et al. |
| 5,649,547 A | 7/1997 | Ritchart et al. |
| 5,653,730 A | 8/1997 | Hammersiag |
| 5,665,107 A | 9/1997 | Hammersiag |
| 5,676,689 A | 10/1997 | Kensey |
| 5,681,279 A | 10/1997 | Roper et al. |
| 5,716,375 A | 2/1998 | Fowler |
| 5,725,498 A | 3/1998 | Janzen et al. |
| 5,741,223 A | 4/1998 | Janzen et al. |
| 5,769,086 A | 6/1998 | Ritchart et al. |
| 5,769,813 A | 6/1998 | Peiler et al. |
| 5,775,333 A | 7/1998 | Burbank et al. |
| 5,782,861 A | 7/1998 | Cragg et al. |
| 5,800,389 A | 9/1998 | Burney et al. |
| 5,810,806 A | 9/1998 | Ritchart et al. |
| 5,830,130 A | 11/1998 | Janzen et al. |
| 5,858,008 A | 1/1999 | Capaccio |
| 5,868,762 A | 2/1999 | Cragg et al. |
| 5,902,310 A | 5/1999 | Foerster et al. |
| 5,984,950 A * | 11/1999 | Cragg et al. ............... 606/216 |
| 6,007,563 A | 12/1999 | Nash et al. |
| 6,027,471 A | 2/2000 | Fallon et al. |
| 6,027,482 A | 2/2000 | Imbert |
| 6,071,300 A | 6/2000 | Brenneman et al. |
| 6,071,301 A | 6/2000 | Cragg et al. |
| 6,086,607 A | 7/2000 | Cragg et al. |
| 6,161,034 A | 12/2000 | Burbank et al. |
| 6,162,192 A | 12/2000 | Cragg et al. |
| 6,183,497 B1 | 2/2001 | Sing et al. |
| 6,200,328 B1 | 3/2001 | Cragg et al. |
| 6,296,622 B1 * | 10/2001 | Kurz et al. ............... 604/93.01 |
| 6,315,753 B1 | 11/2001 | Cragg et al. |
| 6,544,197 B2 * | 4/2003 | DeMello ............... 600/585 |
| 6,610,025 B2 | 8/2003 | Berg et al. |
| 6,623,509 B2 * | 9/2003 | Ginn ............... 606/213 |
| 6,984,219 B2 | 1/2006 | Ashby et al. |
| 7,226,467 B2 * | 6/2007 | Lucatero et al. ............... 606/213 |

FOREIGN PATENT DOCUMENTS

| | | |
|---|---|---|
| EP | 0476178 | 3/1992 |
| EP | 0482350 | 4/1992 |
| EP | 0557963 | 2/1993 |
| EP | 0637431 | 11/1994 |
| FR | 2641692 | 7/1990 |
| GB | 1509023 | 4/1978 |
| GB | 1569660 | 6/1980 |
| SU | 782814 | 11/1980 |
| SU | 1088709 A | 4/1984 |
| WO | WO 91/12847 | 9/1991 |
| WO | WO 94/02072 | 2/1994 |
| WO | WO 94/28800 | 12/1994 |
| WO | WO 95/28124 | 10/1995 |
| WO | WO 95/32669 | 12/1995 |
| WO | WO 95/32671 | 12/1995 |
| WO | WO 96/08208 | 3/1996 |
| WO | WO 96/24290 | 8/1996 |
| WO | WO 98/06346 | 2/1998 |
| WO | WO 99/66834 | 12/1999 |

OTHER PUBLICATIONS

John T. Correll, et al., A new Physiologically absorbable sponge.
John T. Correll, et al. Biologic investigations of new absorbable sponge; p. 585.
Fandrich, C., et al. "Small guage gelfoam plug liver biopsy in high risk patients", Australian Radiology, vol. 230-234 (1996).
Journal of interventional cardiology vol. 5 No. 2 June.
Pharmacia & Upjohn manufacturer brochure "gelfoam sterile powder", (Feb. 1996).
Sanborn, T. Multicenter randomized trial comparing perutaneous collagen hemostasis device with conventional manual compression after diagnostic angiography and angioplasty, J. Am. Coll. Card., vol. 22, pp. 1273-1279, (1993).
Schievink, et al. The new england journal of medicaine; review articles; intracianal aneurysms; Jan. 2, 1997.

Scharader, R. "Collagen appl.", Catheterization & cardiovascular diagnosis (1992) pp. 298-302.

Silber, S., "Rapid hemostasis of arterial puncture sites with collagen in patients undergoing diagnostic interventional cardiac catherterization", clinical cardiology, vol. 20, pp. 981-992, (1997).

Smith, T., "Percutaneous transhepatic liver biopsy with tract embolization", Radiology, vol. 198, pp. 769-774 (1996).

Szikora, et al. Combined Use of stents and cells to treat experimental wide-necked carotid aneuryms: Preliminary results; AJNR AM newradiol 15: 1091-1102, Jun. 1994.

Szikora, et al. Endovascular treatment of experimental anuerysms with liquid polymers: vol. 38, No. 2, Feb. 1996.

Turjman, et al. Combined stent implantation & endosacular coil placement for tretment of experimental wide-necked aneurysms: AJNRAM J. Neuroradio 15: 1087-1090 Jun. 1994.

Yoshimoto, et al cerebral anuerysms unrelated to arterial bifurcations; Acta neurochir (Wien) (96) 138: 958-964.

Zins, M., "US-guided percutaneous liver biopsy with plugging of the needle track" radiology, vol. 187, pp. 841-843,(1992).

Allison, D., et al., "Percutaneous liver biopsy and track embolization with steel coils", Radiology, vol. 169, pp. 261-263, (1998).

J. Bryne Review Article: Endovascular treatments for intracranial anuerysms, 1996 The British journal of radiology; 98,891-899.

Chuang, V., et al., "Sheath needle for liver biopsy in high-risk patience", Radiology, vol. 166, pp. 261-262 (1988).

John T. Correll, et al., A new Physiologically absorbable sponge, Mar. 1945.

John T. Correll, et al. Biologic investigations of new absorbable sponge; p. 585, 1945.

Fandrich, C., et al. "Small guage gelfoam plug liver biopsy in high risk patients", Australian Radiology, vol. 40, pp. 230-234 (1996).

Foran, JPM, et al. "Early mobilisation after percutaneous cardiac catheterisation using collagen plug (vasoseal) maemostatis" BRHeart, vol. 69, pp. 424-429 (1993).

Gibbs, JSR, "Femoral arterial hemostasis" J. Interventional card, vol. 5, pp. 85-88 (1992).

Journal of interventional cardiology vol. 5 No. 2 Jun.

Kassell, et al. Size of Intracanial aneurysm; vol. 12, No. 3, (1983).

Kiemeneiji, F, et al., "Improved anticoagulation management after Palmaz Schatz coronary stent implantation by sealing the arterial puncture site with vascular hemostasis device", Catheterization and Cardiovascular diagnosis, vol. 30, pp. 1685-1692 (1995).

Kussmaul, WG, "Rapid arterial hemostasis", J. Am. Coll. Card., vol. 25, pp. 1685-1692 (1995).

Pharmacia & Upjohn manufacturer brochure gelfoam sterile sponge, sterile powder and sterile film, pp. 1-34 (May 1997).

Pharmacia & Upjohn manufacturer brochure "gelfoam sterile powder ", (Feb. 1996).

Pharmacia & Upjohn manufacturer brochure, "gelfoam sterile powder" (Mar. 1996).

Pharmacia & Upjohn manufacturer brochure (Sep. 1996).

Pharmacia & Upjohn manufacturer specification, "Gelfoam sterile sponge, sterile powder and sterile film" pp. 1-23 (Nov. 1996).

Riley, SA, Percutaneous liver biopsy with plugging of needle track: a safe method for use in patients with impaired coagulation, The lancet, p. 436 (1964).

Sanborn, T. Multicenter randomized trial comparing perutaneous collagen hemostasis device with conventional manual compression after diagnostic angiography and angioplasty, J. Am. Coll. Card., vol. 22, pp. 1273-1279, (1993).

* cited by examiner

RELEASE MECHANISM

CROSS-REFERENCE TO RELATED APPLICATIONS

This application is a continuation-in-part of: (1) prior application Ser. No. 10/287,922, filed Nov. 4, 2002, now issued U.S. Pat. No. 7,455,680; (2) prior application Ser. No. 10/462,065, filed Jun. 12, 2003, now issued U.S. Pat. No. 7,695,492; and (3) prior application Ser. No. 10/461,587, filed Jun. 12, 2003, now issued U.S. Pat. No. 7,955,353. Each of the prior applications noted above is incorporated by reference herein.

FIELD OF THE INVENTION

The present invention relates to a releasable mechanism. More particularly, the present invention relates to a releasable mechanism to provide a low force and stable way to release a hemostatic material.

BACKGROUND OF THE INVENTION

A large number of diagnostic and interventional procedures involve the percutaneous introduction of instrumentation into a vein or artery. For example, coronary angioplasty, angiography, atherectomy, stenting of arteries, and many other procedures often involve accessing the vasculature through a catheter placed in the femoral artery or other blood vessel. Once the procedure is completed and the catheter or other instrumentation is removed, bleeding from the punctured artery must be controlled.

Traditionally, external pressure is applied to the skin entry site to stem bleeding from a puncture wound in a blood vessel. Pressure is continued until hemostasis has occurred at the puncture site. In some instances, pressure must be applied for up to an hour or more during which time the patient is uncomfortably immobilized. In addition, a risk of hematoma exists since bleeding from the vessel may continue beneath the skin until sufficient clotting effects hemostasis. Further, external pressure to close the vascular puncture site works best when the vessel is close to the skin surface but may be unsuitable for patients with substantial amounts of subcutaneous adipose tissue since the skin surface may be a considerable distance from the vascular puncture site.

There are several approaches to close the vascular puncture site including the use of non-absorbable tissue adhesives, absorbable material such as collagen, or anchor and plug systems. The use of either of the approaches above requires the ability to accurately locate the puncture site, position the hemostasis material at or near the puncture site, and release the hemostasis device. However, when releasing the hemostasis material at the puncture site and withdrawing other devices out of the tissue tract, the user typically must pull or tug on the devices which may reposition the hemostasis material or cause damage to the surrounding tissue or vascular puncture site.

Thus, there is still a need for an apparatus and method to efficiently and easily release the hemostasis device and remove any other devices from the puncture site without repositioning the hemostasis material or causing damage to the surrounding tissue or vascular puncture site.

BRIEF DESCRIPTION OF THE INVENTION

The present invention provides for a method and apparatus related to a releasable mechanism having a first connector having a first end and a second end, a second connector having a top and a bottom, a first notch positioned near the first connector second end to releasably mate with the second connector bottom, and a second notch located near the second connector bottom to releasably receive the first connector second end.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

In the drawings:

FIG. 1D is an illustration of the releasable mechanism of FIGS. 1A and 1B in a detached mode.

DETAILED DESCRIPTION

Embodiments of the present invention are described herein in the context of a releasable mechanism. Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings. The same reference indicators will be used throughout the drawings and the following detailed description to refer to the same or like parts.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure Providing hemostasis at the blood vessel puncture site is important for procedures such as puncture closure. Thus, the present invention is directed to a method and apparatus to efficiently and easily release the hemostasis device and remove any other devices from the puncture site without repositioning the hemostasis material or causing damage to the surrounding tissue or vascular puncture site.

Figure 1A:
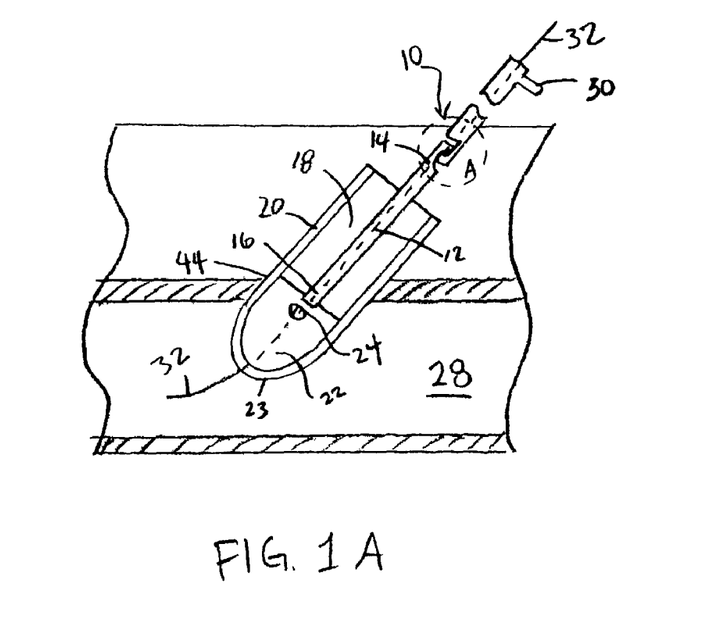
FIGS. 1A and 1B illustrate a releasable mechanism in accordance with an embodiment of the present invention.
Figure 1B:
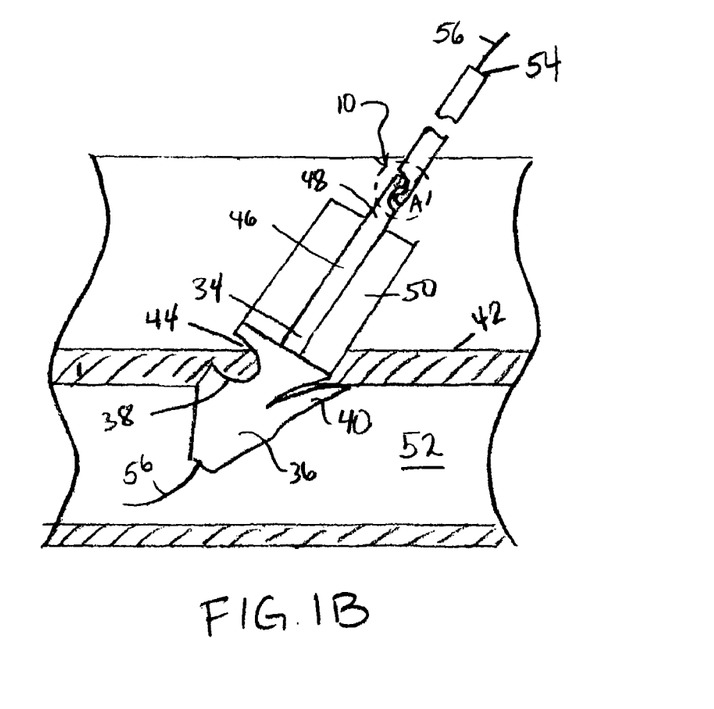

Referring now to FIGS. 1A and 1B, which illustrate a releasable mechanism in accordance with an embodiment of the present invention, FIG. 1A illustrates the releasable mechanism, generally numbered 10, in use with a dissolvable closure device as further described in co-pending patent application Ser. No. 10/461,587, filed on Jun. 12, 2003. However, a brief description will be provided herein. The dissolvable closure device has a communication tube 12 with a top 14 and a bottom 16. A sponge 18 may be positioned around the communication tube bottom 16 and a sponge cover 20 surrounds the sponge 18 thereby forming a hollow distal dip cavity 22. The distal tip 23 may have a bleed back entrance port 24 that is in fluid communication with the communication tube 12. When the device is within the blood vessel lumen 28, blood will flow from the bleed back entrance port 24, through the communication tube 12, and out of a bleed back exit port 30. A guidewire 32 may be positioned through the lumen of the communication tube 12. The releasable mechanism 10 is positioned near the communication tube top 15 and will be further discussed below with reference to FIG. 1C.

FIG. 1B illustrates the releasable mechanism 10 in use with another closure device as further described in co-pending patent application Ser. No. 10/462,065, filed on Jun. 12, 2003. However a brief description will be described herein. The closure device has a communication tube 46 with a top 48 and a bottom 34. A sponge 50 may be positioned around the communication tube bottom 34. Additionally, a guidewire 56 may be received within the communication tube lumen 46.

A distal tip 36 is connected to the communication tube bottom 34 and has a bleed back entrance port 38 and a finger 40. The bleed back entrance port 38 is in fluid communication with the communication tube 46. When the bleed back entrance port 38 is located within the blood vessel lumen 52, blood flows into the bleed back entrance port 38, through the communication tube 46, and out a bleed back exit port 54. When the device is withdrawn, the finger 40 catches on the blood vessel wall 42 which thereby notifies the user that the closure device is located at the blood vessel puncture site 44. It will be appreciated that the distal tip 36 may only have the finger 40 and no bleed back entrance port 38. In this embodiment, the user will rely on retention of the distal tip 36 and the finger 40 to provide tactile feed back. The releasable mechanism 10 is positioned near the communication tube top 48 and will be further discussed below with reference to FIG. 1C.

Figure 1C:
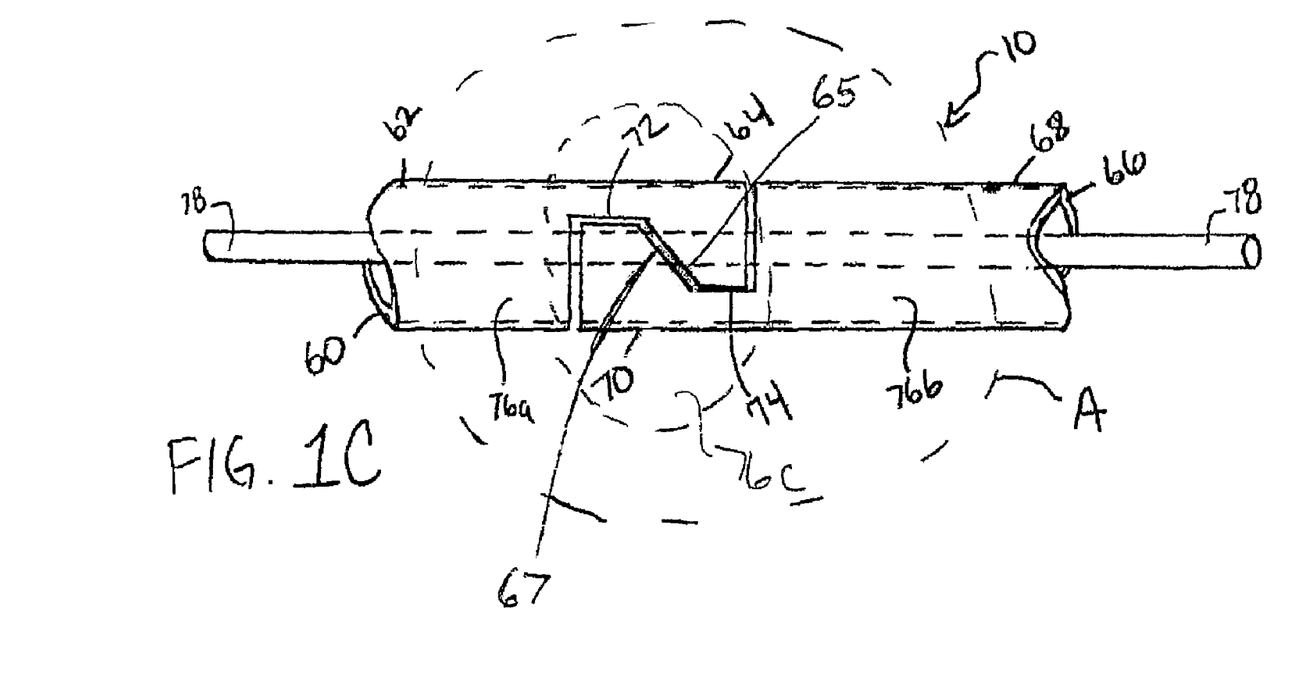
FIG. 1C is an illustration of section A of FIGS. 1A and 1B.

Referring now to FIG. 1C, an illustration is provided of view A of FIGS. 1A and 1B. A distal section of the communication tube 18 or 46 has a first connector 60 having a first end 62 and a second end 64, while a proximal section of the communication tube 18 or 46 includes a second connector 66 having a top 68 and a bottom 70. The first connector 60 has a first notch 72 near the second end 64 to releasably mate with the second connector bottom 70. The second connector 66 has a second notch 74 near the bottom 70 to releasably mate with the first connector second end 64. The first connector 60 and the second connector 66 may have lumens 76a and 76b respectively therethrough to receive a guidewire 78 or any other device. The first notch 72 of the first connector 60 is partially bounded by a first mating wall 65, while the second notch 74 of the second connector 66 is partially bounded by a second mating wall 67 that is complementary to the first mating wall 65. As shown in FIGS. 1C and 1D, the first and second mating walls 65, 67 are inclined at an acute angle with respect to the axes of the lumens 76a and 76b. Notches 72 and 74 may partially or completely interrupt lumens 76a and 76b within their respective first and second connectors in some configurations. The mating of the first connector 60 notch 72 with the second connector bottom 70 and second connector 66 notch 74 with first connector 60 second end 64 completes an intermediate lumen 76c by joining overlapping residual portions of lumens 76a, 76b. After the first connector 60 is mated with the second connector 66, the guidewire 78 is placed through the releasable mechanism by passing through lumens 76a-76c-76b. The guidewire 78 will assist in preventing the first connector and the second connector from separating but will allow the releasable mechanism to move axially along the length of the guidewire.

FIG. 1D is an illustration of the releasable mechanism of FIGS. 1A, 1B, and 1C in a detached mode. Once the closure device of FIGS. 1A and 1B is positioned at the blood vessel puncture site 44, the guidewire 78 is withdrawn and the closure device may easily be removed by detaching the second connector bottom 70 from the first notch 72 and the first connector second end 64 from the second notch 74. The releasable mechanism may be detached by a gentle pull or by twisting the releasable mechanism such that the the first inclined wall 65 slides over and is deflected by the second inclined wall 67 until the first connector second end 64 is removed from the second notch 74 and, simultaneously, the second connector bottom 70 is removed from the first notch 72. Those of ordinary skill in the art will now realize that there may be different ways to release the mechanism. This provides for a low force, stable way to release the sponge 18 or 50 at the blood vessel puncture site 44 and withdraw devices such as a guidewire 78.

Figure 2A:
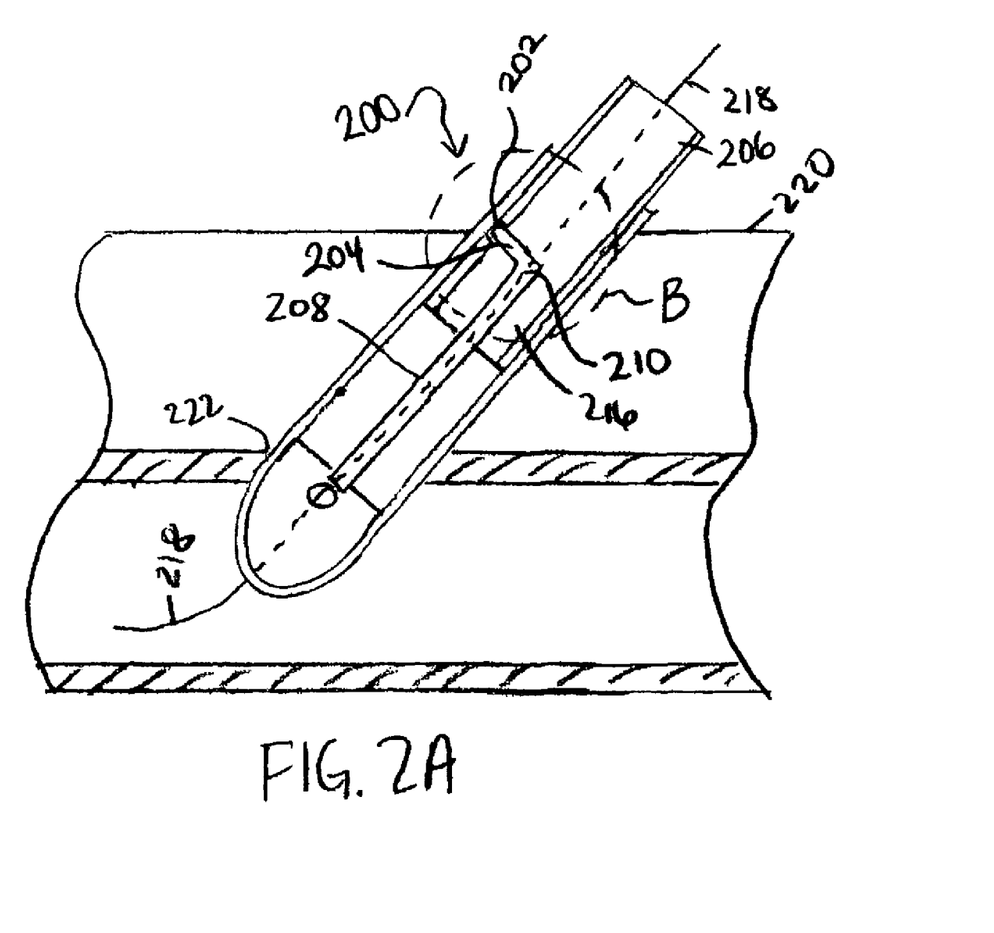
FIGS. 2A, 2B and 2C illustrate a releasable mechanism in accordance with another embodiment of the present invention.
Figure 2B:
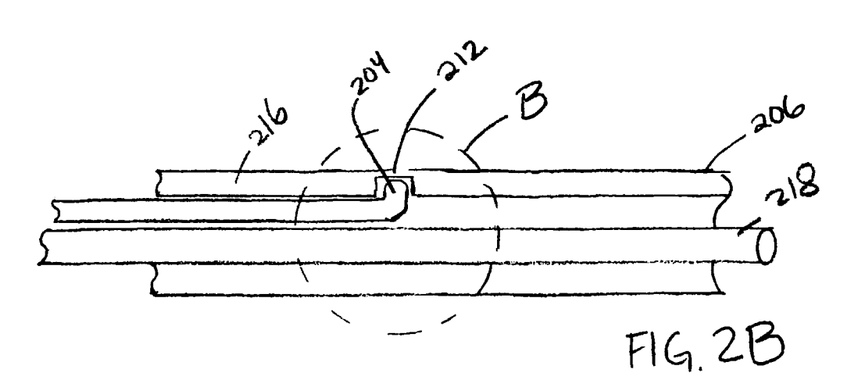
Figure 2C:
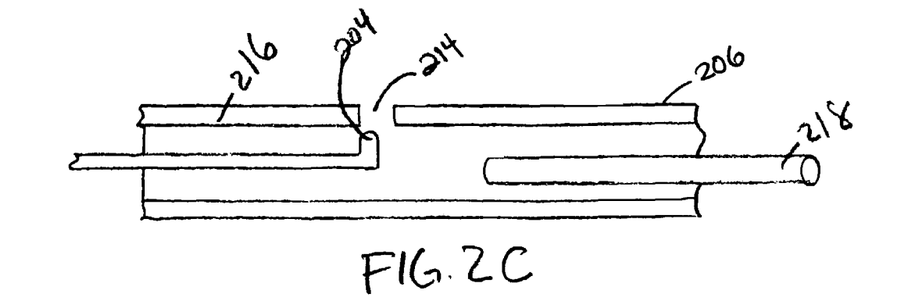
Figure 2D:
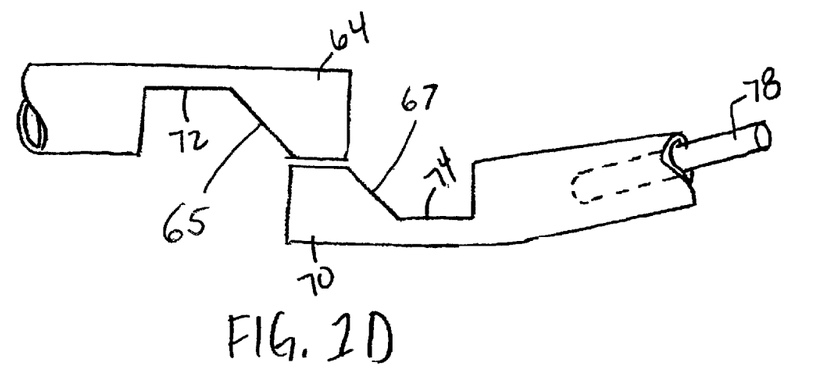

FIGS. 2A, 2B and 2C illustrate a releasable mechanism in accordance with another embodiment of the present invention. FIG. 2A illustrates the release mechanism 200 in use with a closure device having a placement tube 206. The placement tube 206 has a recess 202 in its wall to mate with a foot 204 of the closure device. The foot 204 may be attached to the closure device through various means such as at the top 210 of a communication tube 208. The recess 212 may extend partially into the wall of the placement tube 206 as shown in FIG. 2B or the recess 214 may extend through the entire wall of the placement tube 206 as shown in FIG. 2C. The recess 202, 212, or 214 is preferably located near the placement tube bottom 216, but may be positioned at any location along the placement tube 206.

FIGS. 2B and 2C illustrate the use of the releasable mechanism and further illustrates view B of FIG. 2A. The closure device is positioned over a guidewire 218 and then inserted into the patient's skin 220. As shown in FIG. 2B, the foot 204 is held and engaged within the recess 212 by the guidewire 218. Once the closure device is positioned at the puncture site 222, the closure device may be released by removing the guidewire 218 as shown in FIG. 2C. Removing the guidewire will cause the foot 204 to disengage from the recess 214. Thus, this provides for an efficient and easy release mechanism to release the closure device without any tugging or pulling that may reposition the hemostasis material or cause damage to the surrounding tissue or puncture site.

Figure 3A:
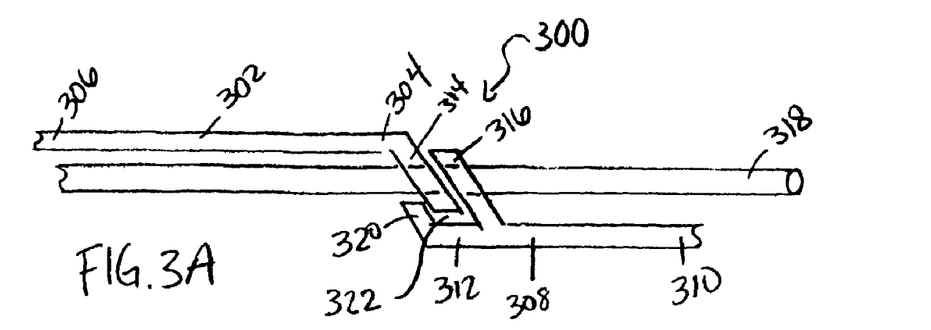
FIGS. 3A, 3B and 3C illustrate a releasable mechanism in accordance with another embodiment of the present invention.
Figure 3B:
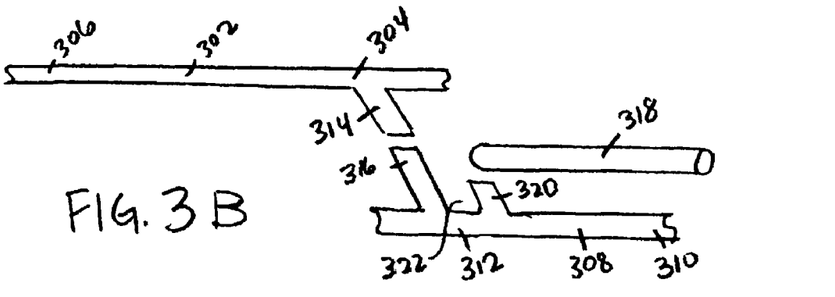

FIGS. 3A and 3B illustrate a releasable mechanism in accordance with another embodiment of the present invention in an attached and detached mode, respectively. The releasable mechanism 300 has a first connector 302 having a first end 304 and a second end 306 and a second connector 308 having a top 310 and a bottom 312. The first connector first end 304 is coupled to a closure device (not shown) similar to those illustrated in FIGS. 1A, 1B, and 2A. The second connector top 310 may extend beyond a patient's skin to allow a user to release the release mechanism from the closure device.

The first connector second end 304 has a first ring 314 positioned at an angle away from the second end 304. The second connector 308 has a projection 320 parallel to a second ring 316 near the bottom 312 such that the projection 320 and the second ring 316 form a recess 322 to releasably mate with the first ring 314. The projection 320 is shorter in length that the second ring 316. Both the first ring 314 and the second ring 316 have a lumen to receive a guidewire 318.

Figure 3C:
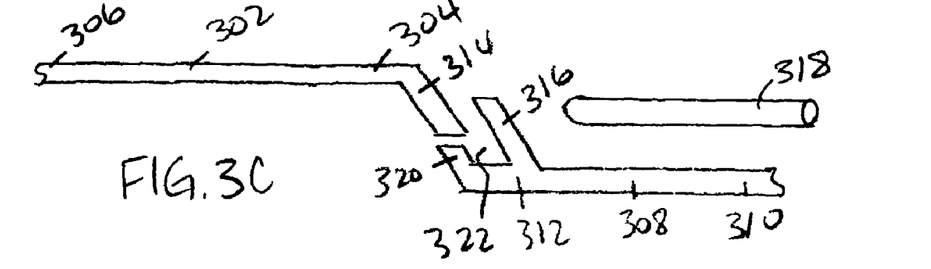

As shown in FIG. 3B, the location of the first ring 314, second ring 316, and projection 320 are not meant to be limiting. For example, the projection 320 may be in front of the second ring 316 as shown in FIG. 3B or may be behind the second rind 316 as shown in FIG. 3C. Additionally, the first ring 314 may be located at the second end 304 as illustrated in FIG. 3C or may be located near the second end 304 as illustrated in FIG. 3B. Thus, those of ordinary skill in the art will now realize that there are many different placements for the first ring, second ring, and projection.

In use, the first ring 314 is positioned within the recess 322 and the guidewire 318 is positioned through the lumen of the first ring 314 and second ring 316. The guidewire 318 will assist in preventing the first connector 302 and the second connector 308 from separating but will allow the releasable mechanism to move axially along the length of the guidewire 318. Once the closure device is positioned at the puncture site, the guidewire 318 is removed and the first ring 314 may be released from the recess 322 with a gentle tug or twist such that the first ring 314 is no longer within the recess 322 as shown in FIGS. 3B and 3C.

The releasable mechanism illustrated in the figures is a cylindrical or rod shaped. However, those of ordinary skill in the art will now realize that the releasable mechanism may be any shape such as a rod, square, or other shape. Additionally, the embodiments described above were illustrated with reference to a puncture closure device used with a guidewire. However, those of ordinary skill in the art will realize that there are other applications the releasable mechanism may be applied with such as with neurological surgery devices and coils.

While embodiments and applications of this invention have been shown and described, it would be apparent to those skilled in the art having the benefit of this disclosure that many more modifications than mentioned above are possible without departing from the inventive concepts herein. The invention, therefore, is not to be restricted except in the spirit of the appended claims.

What is claimed is:

1. An apparatus to provide hemostasis at a blood vessel puncture site, comprising:
    a communication tube having a lumen, a top and bottom;
    a hemostatic material positioned around said communication tube bottom, said hemostatic material having a first end and a second end;
    a hemostatic material cover positioned around the hemostatic material, wherein said hemostatic material cover forms a hollow distal tip cavity at the hemostatic material first end, further wherein said hemostatic material cover comprises a bleed back entrance port in fluid communication with the communication tube;
    a releasable mechanism at said communication tube top, the releasable mechanism including:
        a first connector;
        a second connector;
        said first connector having a first end and a second end, a first connector lumen extending from the first connector first end to the first connector second end, said first connector lumen being in fluid communication with said communication tube lumen;
        a first notch positioned near the first connector second end to releasably mate with the second connector, said first notch partially interrupting said first connector lumen;
        said second connector having a top, a bottom, and a second connector lumen extending from the second connector top to the second connector bottom;
        a second notch located near the second connector bottom to releasably mate with the first connector, said second notch partially interrupting said second connector lumen;
        wherein the first notch is partially bounded by a first mating wall inclined at an acute angle with respect to a longitudinal axis of the first connector lumen and the second notch is partially bounded by a second mating wall inclined at an acute angle with respect to a longitudinal axis of the second connector lumen, such that the first and second mating walls are complementary to each other;
        wherein the mating of the first connector second end with the second connector second notch and the second connector bottom with the first connector first notch defines a series of lumens in continuous fluid communication extending from the hemostatic material cover bleed back entrance port to the second connector top.

2. The apparatus of claim 1 further comprising a guidewire received by said first connector lumen and said second connector lumen.

3. The apparatus of claim 2, wherein when the guidewire is received by said first connector lumen and said second connector lumen, fluid communication is maintained between the hemostatic material cover bleed back entrance port and the second connector top.

4. The apparatus of claim 3, wherein the guidewire is further received by the bleed back entrance port.

5. The apparatus of claim 4, wherein when the guidewire is received by the first connector lumen, the second connector lumen, the communication tube and the bleed back entrance port, fluid communication is maintained between the hemostatic material cover bleed back entrance port and the second connector top.

6. The apparatus of claim 2, wherein the guidewire is further received by the communication tube.

7. The apparatus of claim 6, wherein when the guidewire is received by the first connector lumen, the second connector lumen, and the communication tube, fluid communication is maintained between the hemostatic material cover bleed back entrance port and the second connector top.

8. The apparatus of claim 1, wherein the said first notch completely interrupts said first connector lumen.

9. The apparatus of claim 1, wherein the said second notch completely interrupts said second connector lumen.

10. The apparatus of claim 1, wherein the second connector further comprises a bleed back exit port.

* * * * *